(12) United States Patent
Hommeltoft et al.

(10) Patent No.: US 9,084,991 B2
(45) Date of Patent: *Jul. 21, 2015

(54) ACID CATALYST COMPOSITION COMPRISING CONJUNCT POLYMER AND LEWIS ACID

(71) Applicants: Sven Ivar Hommeltoft, Pleasant Hill, CA (US); Howard Steven Lacheen, Richmond, CA (US); Saleh Ali Elomari, Fairfiled, CA (US)

(72) Inventors: Sven Ivar Hommeltoft, Pleasant Hill, CA (US); Howard Steven Lacheen, Richmond, CA (US); Saleh Ali Elomari, Fairfiled, CA (US)

(73) Assignee: Chevron U.S.A., San Ramon, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 13/661,953

(22) Filed: Oct. 26, 2012

(65) Prior Publication Data

US 2013/0053235 A1 Feb. 28, 2013

Related U.S. Application Data

(60) Division of application No. 13/228,171, filed on Sep. 8, 2011, which is a division of application No. 12/335,476, filed on Dec. 15, 2008, and a continuation of application No. 12/335,487, filed on Dec. 15, 2008, now abandoned, and a continuation of application No. 12/335,494, filed on Dec. 15, 2008, now abandoned, and a continuation of application No. 13/228,143, filed on Sep. 8, 2011.

(51) Int. Cl.
*B01J 31/06* (2006.01)
*B01J 31/26* (2006.01)
*C07C 2/58* (2006.01)
*B01J 31/02* (2006.01)

(52) U.S. Cl.
CPC . *B01J 31/06* (2013.01); *C07C 2/58* (2013.01); *B01J 31/0284* (2013.01); *B01J 31/0298* (2013.01); *B01J 2231/32* (2013.01); *C07C 2527/126* (2013.01); *C07C 2531/02* (2013.01); *C07C 2531/06* (2013.01)

(58) Field of Classification Search
CPC . B01J 2231/32; B01J 31/0298; B01J 31/0284
See application file for complete search history.

(56) References Cited

U.S. PATENT DOCUMENTS

| 3,760,022 | A | 9/1973 | Schmerling |
|---|---|---|---|
| 5,406,018 | A | 4/1995 | Sherman |
| 7,285,698 | B2 | 10/2007 | Liu et al. |
| 7,432,408 | B2 | 10/2008 | Timken et al. |
| 7,432,409 | B2 | 10/2008 | Elomari et al. |
| 7,495,144 | B2 | 2/2009 | Elomari |
| 7,732,364 | B2 | 6/2010 | Chang et al. |
| 7,754,636 | B2 | 7/2010 | Elomari et al. |
| 7,807,597 | B2 | 10/2010 | Elomari et al. |
| 7,923,593 | B2 | 4/2011 | Hommeltoft et al. |
| 7,955,999 | B2 | 6/2011 | Luo et al. |
| 7,956,002 | B2 | 6/2011 | Elomari et al. |
| 8,070,939 | B2 | 12/2011 | Hommeltoft et al. |
| 2006/0135839 | A1 | 6/2006 | Elomari et al. |
| 2007/0142211 | A1 * | 6/2007 | Elomari et al. ............ 502/29 |
| 2007/0142213 | A1 | 6/2007 | Elomari et al. |
| 2007/0142214 | A1 | 6/2007 | Elomari et al. |
| 2007/0142215 | A1 | 6/2007 | Harris et al. |
| 2007/0142216 | A1 | 6/2007 | Elomari et al. |
| 2007/0142217 | A1 | 6/2007 | Elomari et al. |
| 2007/0142218 | A1 * | 6/2007 | Harris et al. ............ 502/53 |
| 2007/0142676 | A1 | 6/2007 | Elomari et al. |
| 2007/0142686 | A1 | 6/2007 | Campbell et al. |
| 2007/0225538 | A1 * | 9/2007 | Elomari ............ 585/727 |
| 2007/0249485 | A1 * | 10/2007 | Elomari et al. ............ 502/20 |
| 2008/0085754 | A1 | 4/2008 | Okada |

FOREIGN PATENT DOCUMENTS

| CN | 1137536 A * | 12/1996 | ............ C08F 240/00 |
|---|---|---|---|
| WO | WO9521871 | 8/1995 | |

OTHER PUBLICATIONS

PCT/US2009/064751, Notification Concerning Transmittal of International Preliminary Report on Patentability, Jun. 30, 2011, 6 pages.
Yves Chauvin, et al., Alkylation of isobutene with 2-butene using 1 butyl 3-methylimidazolium chloride aluminum chloride molten salts as catalysis, Journal of Molecular Catalysis, 1994, pp. 155-165, 92, Elsevier.
Zhao, et al., Effects of kinds of ionic liquid catalysts on alkylation of 1 and2 methylnaphthalene with alkenes, Applied Catalysis A: General, 2005 pp. 133-137, 290, Elsevier.
U.S. Appl. No. 61/118,215 "Electrochemical removal of conjunct polymers from chloroaluminate ionic liquids", filed Nov. 26, 2008, Timken, et al.
Rebeiro, et al., Chloroaluminate ionic liquid for Fischer indole synthesis, Synthesis, 2001, No. 3, pp. 370-372.
PCT/US2009/064751, International Search Report, mailing date Jul. 2, 2010, pp. 1-3.
Moir, et al., Molecular Structure of Conjunct Polymers, J. Chem. & Engg. Data 1963 150-160.

* cited by examiner

*Primary Examiner* — Yun Qian
(74) *Attorney, Agent, or Firm* — Susan M. Abernathy

(57) ABSTRACT

An acid catalyst effective for a conversion of a hydrocarbon, comprising: greater than 15 wt % halide-containing conjunct polymer, and a Lewis acid; wherein less than 0.1 wt % solid precipitates from the catalyst when it is held for three hours or longer at 25° C. or below.

9 Claims, No Drawings

ACID CATALYST COMPOSITION COMPRISING CONJUNCT POLYMER AND LEWIS ACID

This application is a division of prior application Ser. No. 13/228,171, filed Sep. 8, 2011, and published as US 2012-0004095 A1, herein incorporated by reference in its entirety. The assigned art unit of the prior parent application is 1732.

This application is also a division of prior application Ser. No. 12/335,476, filed Dec. 15, 2008, and published as US 2010-0152506 A1, herein incorporated by reference in its entirety. The assigned art unit of the second prior parent application is 1732.

This application also claims the benefit as a continuation to two previously co-filed patent applications titled "IONIC LIQUID CATALYST HAVING A HIGH MOLAR RATIO OF ALUMINUM TO NITROGEN," published as US20100152027A1, and "PROCESS TO MAKE A LIQUID CATALYST HAVING A HIGH MOLAR RATIO OF ALUMINUM TO NITROGEN," published as US20100152518A1, herein incorporated by reference in their entireties.

This application is also a continuation to a previously co-filed application titled "A METHOD TO MAKE AN ACID CATALYST HAVING GREATER THAN 20 WT % CONJUNCT POLYMER", published as US20110319258A1, herein incorporated by reference in its entirety.

This application is related to a co-filed application titled "AN ACID CATALYST COMPOSITION COMPRISING HALIDE-CONTAINING CONJUNCT POLYMER AND LEWIS ACID" herein incorporated in its entirety.

FIELD OF THE INVENTION

This invention is directed to an acid catalyst composition that is effective for conversion of a hydrocarbon having greater than 15-20 wt % conjunct polymer.

DETAILED DESCRIPTION OF THE INVENTION

In one embodiment, a process for hydrocarbon conversion, comprising: contacting a hydrocarbon with an acid catalyst containing greater than 15 wt % conjunct polymer is provided; wherein the acid catalyst has a molar ratio of Al to a heteroatom selected from the group of N, P, O, S, and combinations thereof greater than 2.0; and wherein the hydrocarbon is converted during the contacting.

In another embodiment, a method to make a catalyst is provided, comprising: mixing aluminum chloride in the presence of a hydrocarbon solvent and an organic chloride and optionally an ionic liquid; whereby the resulting acidic ionic liquid catalyst has greater than 15 wt % conjunct polymer and has a molar ratio of Al to a heteroatom selected from the group consisting of N, P, O, S, and combinations thereof greater than 2.0. The resulting ionic liquid catalyst is effective for catalyzing a reaction.

Additionally, there is provided an acid catalyst composition, comprising greater than 15 wt % conjunct polymer and having a molar ratio of Al to a heteroatom selected from the group consisting of N, P, O, S, and combinations thereof greater than 2.0. The catalyst is effective for a conversion of a hydrocarbon.

Also, an acid hydroconversion catalyst is provided, comprising greater than 15 wt % halide-containing conjunct polymer and a Lewis acid; wherein less than 0.1 wt % solid precipitates from the catalyst when it is held for three hours or longer at 25° C. or below.

Definitions:

The term "comprising" means including the elements or steps that are identified following that term, but any such elements or steps are not exhaustive, and an embodiment may include other elements or steps.

The term "effective for catalyzing a reaction" means that a commercially sufficient amount of a hydrocarbon is converted by a reaction. The term "effective for conversion of a hydrocarbon" also means a commercially sufficient amount of the hydrocarbon is converted. For example, in an isoparaffin/olefin alkylation this could be greater than 75 wt % conversion of an olefin, greater than 85 wt % conversion of an olefin, greater than 95 wt % conversion of an olefin, or up to 100 wt % conversion of an olefin. The commercially significant amount can vary substantially depending on the hydrocarbon being converted and the value of the converted product that is produced.

The term conjunct polymer was first used by Pines and Ipatieff to distinguish these polymeric molecules from typical polymers. Unlike typical polymers which are compounds formed from repeating units of smaller molecules by controlled or semi-controlled polymerizations, "conjunct polymers" are "pseudo-polymeric" compounds formed asymmetrically from two or more reacting units by concurrent acid-catalyzed transformations including polymerization, alkylation, cyclization, additions, eliminations and hydride transfer reactions. Consequently, the produced "pseudo-polymeric" may include a large number of compounds with varying structures and substitution patterns. The skeletal structures of "conjunct polymers", therefore, range from the very simple linear molecules to very complex multi-feature molecules.

Some examples of the likely polymeric species in conjunct polymers were reported by Miron et al. (Journal of Chemical and Engineering Data, 1963), and Pines (Chem. Tech, 1982). Conjunct polymers are also commonly known to those in the refining industry as "red oils" due to their reddish-amber color or "acid-soluble oils" due to their high uptake in the catalyst phase where paraffinic products and hydrocarbons with low olefinicity and low functional groups are usually immiscible in the catalyst phase. In this application, the term "conjunct polymers" also includes ASOs (acid-soluble-oils), red oils, and C12+ polyalkylates.

In one embodiment the acid catalyst is a solid. Examples of solid acid catalysts are supported catalysts, supported Lewis acid catalysts, H-form zeolites, mass sulfated zirconia catalysts, zirconium oxide catalysts, solid phosphoric acid catalysts, crystalline tin oxide, supported sulfonic acids, and heteropoly acids.

In one embodiment the acid catalyst is a liquid. Examples of liquid catalysts are sulfuric acid or hydrofluoric acid. In another embodiment the liquid acid catalyst is an ionic liquid catalyst.

Ionic Liquid Catalyst:

"Ionic liquids" are liquids whose make-up is comprised of ions as a combination of cations and anions. The most common ionic liquids are those prepared from organic-based cations and inorganic or organic anions. Ionic liquid catalysts are used in a wide variety of reactions, including Friedel-Crafts reactions.

The ionic liquid catalyst is composed of at least two components which form a complex. To be effective at alkylation the ionic liquid catalyst is acidic. The ionic liquid catalyst comprises a first component and a second component. The first component of the catalyst will typically comprise a Lewis acid compound selected from components such as Lewis acid compounds of Group 13 metals, including aluminum halides, alkyl aluminum halide, gallium halide, and alkyl gallium halide (see International Union of Pure and Applied Chemistry (IUPAC), version3, October 2005, for Group 13 metals of the periodic table). Other Lewis acid compounds besides those of Group 13 metals may also be used. In one embodiment the first component is aluminum halide or alkyl aluminum halide. For example, aluminum trichloride ($AlCl_3$) may be used as the first component for preparing the ionic liquid catalyst.

The second component making up the ionic liquid catalyst is an organic salt or mixture of salts. These salts may be characterized by the general formula Q+A−, wherein Q+ is an ammonium, phosphonium, boronium, oxonium, iodonium, or sulfonium cation and A− is a negatively charged ion such as Cl−, Br−, $ClO_4^-$, $NO_3^-$, $BF_4^-$, $BCl_4^-$, $PF_6^-$, $SbF_6^-$, $AlCl_4^-$, $Al_2Cl_7^-$, $Al_3Cl_{10}^-$, $ArF_6^-$, $TaF_6^-$, $CuCl_2^-$, $FeCl_3^-$, $SO_3CF_3^-$, $SO_3C_7^-$, and 3-sulfurtrioxyphenyl. In one embodiment the second component is selected from those having quaternary ammonium halides containing one or more alkyl moieties having from about 1 to about 9 carbon atoms, such as, for example, trimethylammonium hydrochloride, methyltributy-lammonium, 1-butyl pyridinium, or alkyl substituted imidazolium halides, such as for example, 1-ethyl-3-methyl-imidazolium chloride.

In one embodiment the ionic liquid catalyst is a quaternary ammonium chloroaluminate ionic liquid having the general formula RR' R" N H+ $Al_2Cl_7^-$, wherein RR' and R" are alkyl groups containing 1 to 12 carbons. Examples of quaternary ammonium chloroaluminate ionic liquid salts are an N-alkyl-pyridinium chloroaluminate, an N-alkyl-alkylpyridinium chloroaluminate, a pyridinium hydrogen chloroaluminate, an alkyl pyridinium hydrogen chloroaluminate, a di-alkyl-imidazolium chloroaluminate, a tetra-alkyl-ammonium chloroaluminate, a tri-alkyl-ammonium hydrogen chloroaluminate, or a mixture thereof.

The presence of the first component should give the ionic liquid a Lewis or Franklin acidic character. Generally, the greater the mole ratio of the first component to the second component, the greater is the acidity of the ionic liquid mixture.

For example, a typical reaction mixture to prepare n-butyl pyridinium chloroaluminate ionic liquid salt is shown below:

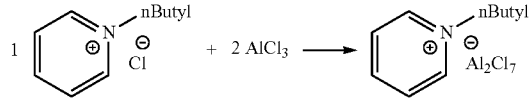

The molar ratio of Al to the heteroatom is greater than 2.0 when the acid catalyst is held at a temperature at or below 25° C. for at least two hours.

In different embodiments the molar ratio of Al to the heteroatom is about 5 or greater, about 10 or greater, about 50 or greater, or even greater than 100. In some embodiments there is little or no heteroatom, so the molar ratio of Al to the heteroatom can be about 10 to about 1000, or even higher.

The acid catalyst comprises greater than 15 wt % conjunct polymer. The high level of conjunct polymer in the catalyst increases the catalyst's capacity to uptake acids, such as $AlCl_3$. In different embodiments the acid catalyst comprises greater than 20 wt % conjunct polymer, greater than 25 wt % conjunct polymer, greater than 30 wt % conjunct polymer, greater than 40 wt % conjunct polymer, or greater than 50 wt % conjunct polymer.

The contacting may occur at any temperature known to produce good hydrocarbon conversion. These temperatures can range from about −20° C. up to about 500° C. For isoparaffin/olefin alkylation using an ionic liquid catalyst the temperature can range from about −20° C. up to about 200° C. In different embodiments the temperature can be from −10° C. to 100° C., from 0° C. to 50° C., or below 25° C.

In one embodiment the acid catalyst is made with reagents having no nitrogen-containing compounds.

In another embodiment the acid catalyst is made from at least one conjunct polymer and a Lewis acid. $AlCl_3$ is one example of a useful Lewis acid. In yet another embodiment the acid catalyst is made from at least one conjunct polymer, $AlCl_3$, and hydrogen chloride. The conjunct polymer can comprise a halide. Examples of halides are fluorine, chlorine, bromine, iodine, and combinations thereof.

The level of conjunct polymer in the acid catalyst is determined by hydrolysis of known weights of the catalyst. An example of a suitable test method is described in Example 3 of commonly assigned U.S. Patent Publication Number US20070142213A1. Conjunct polymers can be recovered from the acid catalyst by means of hydrolysis. The hydrolysis recovery methods employ procedures that lead to complete recovery of the conjunct polymers and are generally used for analytical and characterization purposes because it results in the destruction of the catalyst. Hydrolysis of the acid catalyst is done, for example, by stirring the spent catalyst in the presence of excess amount of water followed by extraction with low boiling hydrocarbon solvents such as pentane or hexane. In the hydrolysis process, the catalyst salt and other salts formed during hydrolysis go into the aqueous layer while conjunct polymers go into the organic solvent. The low boiling solvent containing the conjunct polymers are concentrated on a rotary evaporator under vacuum and moderate temperature to remove the extractant, leaving behind the high boiling residual oils (conjunct polymers) which are collected and analyzed. The low boiling extractants can be also removed by distillation methods.

In one embodiment, the conjunct polymer is extractable. The conjunct polymer may be extracted during a catalyst regeneration process, such as by treatment of the catalyst with aluminum metal or with aluminum metal and hydrogen chloride. Examples of methods for regenerating ionic liquid catalysts are taught in U.S. Patent Publications US20070142215A1, US20070142213A1, US20070142676A1, US20070142214A1, US20070142216A1, US20070142211A1, US20070142217A1, US20070142218A1, US20070249485 A1, and in U.S. patent application Ser. No. 11/960319, filed Dec. 19, 2007; U.S. patent application Ser. No. 12/003577, filed Dec. 28, 2007; U.S. patent application Ser. No. 12/003578, filed Dec. 28, 2007; U.S. patent application Ser. No. 12/099486, filed Apr. 8, 2008; and 61/118215, filed Nov. 26, 2008.

One advantage of the acid catalyst having a molar ratio of Al to a heteroatom selected from the group of N, P, O, S, and combinations thereof greater than 2.0 is its ability to continue to function effectively to convert the hydrocarbon, without becoming significantly deactivated by conjunct polymer. In this embodiment the acid catalyst can be used continuously without having to be removed from the reactor for regeneration for more than 7 days, more than 25 days, or more than 50 days. In this embodiment the acid catalyst may be regenerated in part, such that only a portion of the acid catalyst is regenerated at a time and the hydrocarbon conversion process does not need to be interrupted. For example, a slip stream of the acid catalyst effluent can be regenerated and recycled to the hydrocarbon conversion reactor. In one embodiment the level of the conjunct polymer is maintained within the desired range by partial regeneration in a continuous hydrocarbon conversion process.

Examples of hydrocarbon conversions are alkylation, isomerization, hydrocracking, polymerization, dimerization, oligomerization, acylation, metathesis, copolymerization, hydroformylation, dehalogenation, dehydration, and combinations thereof. In one embodiment the hydrocarbon conversion is isoparaffin/olefin alkylation. Examples of ionic liquid catalysts and their use for isoparaffin/olefin alkylation are taught, for example, in U.S. Pat. Nos. 7,432,408 and 7,432,409, 7,285,698, and U.S. patent application Ser. No. 12/184069, filed Jul. 31, 2008. In another embodiment the conversion of a hydrocarbon is alkylation of paraffins, alkylation of aromatics, or combinations thereof.

In some embodiments the acid catalyst comprising greater than 15 wt % conjunct catalyst remains liquid, and does not precipitate significant amounts of solids when it is held for extended periods of time at 25° C. For example, in one embodiment the Lewis acid remains soluble in the acid catalyst, such that less than 0.5 wt %, less than 0.1 wt %, less than 0.05 wt %, less than 0.01 wt %, or zero wt % of the Lewis acid or other solid precipitates out of the liquid catalyst when it is held for three hours or longer at 25° C. This provides a significant technical advantage over other ionic liquid catalysts that precipitate out solids during use.

The time the catalyst can be held at a temperature at or below 25° C. can be fairly lengthy. In general, the time is for greater than a minute, but it can be much longer, such as for greater than 5 minutes, for at least two hours, three hours or longer, more than 7 days up to two weeks, more than 50 days, several months, or even up to a year.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims.

EXAMPLES

Example 1

An ionic liquid catalyst based on n-butyl pyridinium chloroaluminate, having a molar ratio of Al to N of about 5 was prepared and tested as follows: 10.8 g (81 mmoles) of $AlCl_3$ was combined with 5.0 ml (15 mmoles) of n-butyl pyridinium chloroaluminate ionic liquid salt in 30 ml isopentane. 20 ml (180 mmoles) t-butyl chloride was added over a period of 15 minutes. As the reaction proceeded, the hydrocarbon solution boiled and the temperature dropped to about 2 to 5 °C. After the t-butyl chloride addition ended, the temperature started to climb back up. Most of the added $AlCl_3$ was dissolved, although a small amount still remained undissolved. An additional 10 ml isopentane was added and a GC sample revealed that the hydrocarbon phases consisted of a mixture of saturated isoalkanes predominantly in the C5 to C7 range. After stirring over the weekend, almost all the $AlCl_3$ was dissolved, and the acid catalyst phase contained 24.6 wt % conjunct polymer.

5 ml of the conjunct polymer, prepared above, was cooled to 0° C. At t=0 min., 25 ml of a cold (0° C.) solution of 3.6% 2-pentene in isopentane was added and the mixture was stirred on an ice bath. GC samples of the hydrocarbon phase showed slow olefin conversion. After 15 minutes, about 33 wt % of the olefin was converted. Following the addition of 30 ml gaseous hydrogen chloride (1.2 mmoles) the reaction rate increased dramatically. After an additional 3 minutes, 100% of the olefin was converted. The hydrocarbon phase showed that the olefin conversion was to predominantly C8 to C10 isoalkanes.

Example 2

A liquid acid catalyst made entirely of conjunct polymer, and having no heteroatom-containing compounds containing N, S, O, or P, was prepared and tested. This liquid acid catalyst had a molar ratio of Al to heteroatom selected from N, S, O, P, or combinations thereof much greater than 100.

14.2 g (106 mmoles) $AlCl_3$ was slurried up in 30 ml isopentane at room temperature in a flask. 45 ml (38 g, 410 mmoles) t-butyl chloride was added gradually over about half an hour. Gas evolution was observed. The temperature of the slurry in the flask dropped during addition. Without being bound by theory, it is expected that the temperature drop was caused by evaporating hydrogen chloride and the formation of isobutene in the reaction. After the complete addition of the t-butyl chloride, the flask was allowed to warm back up to room temperature. At this point the flask contained a clear brown somewhat viscous liquid with a very small amount of clear hydrocarbon phase on top. The yield of the clear brown somewhat viscous liquid was 31.9 g. The clear brown somewhat viscous liquid was analyzed and was found to contain 43.5 wt % conjunct polymer. This clear brown somewhat viscous liquid was a conjunct polymer based ionic liquid. Laboratory experience has shown that the conjunct polymer prepared in this manner does not to any significant extent differ from the conjunct polymer formed in ionic liquid catalyzed isobutane alkylation.

5 ml of the conjunct polymer based ionic liquid described above was saturated with hydrogen chloride at 1 atm pressure and reacted with 25 ml of 5% 2-pentene in isopentane at 0° C. as described in Example 3. After 1.5 minutes the olefin conversion was 74 wt %, and after 3 minutes more than 98 wt % of the olefin was converted. The reaction product contained a substantial amount of C9-C11 alkylate. Initially, in this experiment, much of the reacted olefin was converted to a mixture of 2- and 3-pentyl chloride, which subsequently reacted to form the final alkylate product.

Example 3

Two alkylation experiments using different ionic liquid catalysts were run on the same feed, at the same temperature, and for the same length of time. The feed was isopentane and 2-pentenes; the temperature was 0° C.; and the time was 6 minutes. In one experiment the alkylation catalyst was n-butyl pyridinium heptachlorodialuminate. In the second experiment the alkylation catalyst was the same conjunct polymer acid catalyst as described in Example 2 (ASO.HAl2Cl7). The reaction products were collected and analyzed by GC. The GC results are shown below.

| Reaction Conditions: | Ionic Liquid: | |
|---|---|---|
| | NBuPyAL2CL7 (Reference) 6 min, 0° C. | ASO•HAl2Cl7 Example 2 6 min, 0° C. |
| C6 | 15.44 | 22.85 |
| C7 | 4.07 | 11.47 |
| C8 | 3.35 | 5.79 |
| C9 | 10.45 | 12.68 |
| C10 | 33.36 | 32.10 |
| C11+ | 33.33 | 15.11 |

The yields and selectivity of the products were similar between the two experiments. Although the n-butyl pyridinium heptachlorodialuminate hydrocarbon conversion gave a slightly heavier product in this particular experiment, this can be controlled by the adjustment of the hydrogen chloride level during the reaction. The adjustment of the hydrogen chloride level to control product selectivity is described in U.S. patent application Ser. No. 12/233,481, filed Sep. 17, 2008.

What is claimed is:

1. An acid catalyst effective for a conversion of a hydrocarbon, comprising: a molar ratio of a compound containing Al to a compound containing a heteroatom of 5 or greater, greater than 20 wt % halide-containing conjunct polymer, and a Lewis acid; wherein less than 0.1 wt % solid precipitates from the catalyst when it is held for three hours or longer at 25° C. or below; wherein the conversion is an alkylation, an isomerization, a hydrocracking, a polymerization, a dimerization, an oligomerization, an acylation, an acetylation, a metathesis, a copolymerization, a dehalogenation, a dehydration, an olefin hydrogenation, or combinations thereof; wherein at least 33 wt % of the hydrocarbon is converted; wherein the heteroatom is selected from the group of N, P, O, S, and combinations thereof; and wherein the acid catalyst comprises an ionic liquid catalyst made of two components, a first component being a Lewis acid compound of Group 13 metals and a second component being an organic salt characterized by a general formula $Q^+A^-$, wherein $Q^+$ is an ammonium, phosphonium, oxonium, or sulfonium cation and $A^-$ is a negatively charged ion.

2. The acid catalyst of claim 1, wherein the conversion is the alkylation, the oligomerization, or a combination thereof.

3. The acid catalyst of claim 2, wherein the conversion is the alkylation of an isoparaffin with an olefin.

4. The acid catalyst of claim 2, wherein the conversion is the oligomerization.

5. The acid catalyst of claim 1, wherein at least 74 wt % of the hydrocarbon is converted.

6. The acid catalyst of claim 1, additionally comprising a hydrogen chloride.

7. The acid catalyst of claim 1, made by adding an alkyl halide to the Lewis acid, wherein a molar amount of the alkyl halide exceeds a molar amount of the Lewis acid.

8. The acid catalyst of claim 7, wherein the alkyl halide is t-butyl chloride and the Lewis acid is $AlCl_3$.

9. The acid catalyst of claim 1, wherein the Lewis acid is $AlCl_3$.

* * * * *